(12) United States Patent
Wolfman et al.

(10) Patent No.: US 7,559,660 B2
(45) Date of Patent: Jul. 14, 2009

(54) RESTRICTED ACCESS DISPLAY SYSTEM

(75) Inventors: G. Jonathan Wolfman, Southbury, CT (US); Benjamin D Singer, Bridgeport, CT (US); Ronald P. Sansone, Weston, CT (US)

(73) Assignee: Pitney Bowes Inc., Stamford, CT (US)

( * ) Notice: Subject to any disclaimer, the term of this patent is extended or adjusted under 35 U.S.C. 154(b) by 791 days.

(21) Appl. No.: 11/274,580

(22) Filed: Nov. 15, 2005

(65) Prior Publication Data

US 2006/0121372 A1 Jun. 8, 2006

Related U.S. Application Data

(60) Provisional application No. 60/630,692, filed on Nov. 24, 2004.

(51) Int. Cl.
  G03B 21/00  (2006.01)
  G03B 21/22  (2006.01)
  G09F 13/00  (2006.01)

(52) U.S. Cl. .......................... 353/121; 353/119; 40/443; 40/548

(58) Field of Classification Search .................... 353/20, 353/21, 119, 122; 359/483, 484, 485; 430/1, 430/7, 11, 19; 362/29; 40/443, 541, 548, 40/584; 428/10, 29, 31
See application file for complete search history.

(56) References Cited

U.S. PATENT DOCUMENTS

| | | | |
|---|---|---|---|
| 5,488,496 A * | 1/1996 | Pine ............................ 349/96 |
| 6,211,930 B1 * | 4/2001 | Sautter et al. ................. 349/66 |
| 6,269,565 B1 * | 8/2001 | Inbar et al. ..................... 40/361 |
| 6,715,879 B2 * | 4/2004 | De Vaan ....................... 353/20 |
| 6,765,550 B2 * | 7/2004 | Janick et al. .................. 345/87 |
| 6,789,910 B2 * | 9/2004 | Kimura et al. .............. 362/600 |
| 7,319,755 B2 * | 1/2008 | Struyk ......................... 380/213 |
| 2006/0072793 A1 | 4/2006 | Determan |
| 2006/0078179 A1 * | 4/2006 | Hung et al. ................. 382/126 |
| 2006/0088193 A1 | 4/2006 | Muller et al. |
| 2006/0088195 A1 * | 4/2006 | Tykowski et al. ........... 382/124 |
| 2006/0126905 A1 | 6/2006 | Loo |

FOREIGN PATENT DOCUMENTS

JP    07084253    3/1996

* cited by examiner

Primary Examiner—William C Dowling
Assistant Examiner—Danell L Owens
(74) Attorney, Agent, or Firm—Ronald Reichman; Angelo N. Chaclas

(57) ABSTRACT

A board that hides information in a manner that only certain authorized personnel may change the information and other authorized personnel may view the information. This invention accomplishes the foregoing by placing a locked panel of translucent material over certain information written on the board that may only be changed by an authorized individual by opening the lock. A panel of opaque material is placed over the translucent material in a manner that certain information written on the board will be revealed when authorized personnel remove the opaque material or cause the opaque material to be transparent. The translucent material may be removed by activating a switch or entering a code.

9 Claims, 8 Drawing Sheets

| PHYSICIAN | PATIENT | PATIENT INFORMATION | ROOM |
|---|---|---|---|
| SALK | JANE DOE | MENINGITIS – O2 – TRANSFUSION AB POS | 215B |
| FLEMMING | JOHN SMITH | HERNIA | 211A |
| DEBACKEY | FRANK WILLIAMS | MYCOTIC ANEURYSM | 213A |

FIG. 1
PRIOR ART

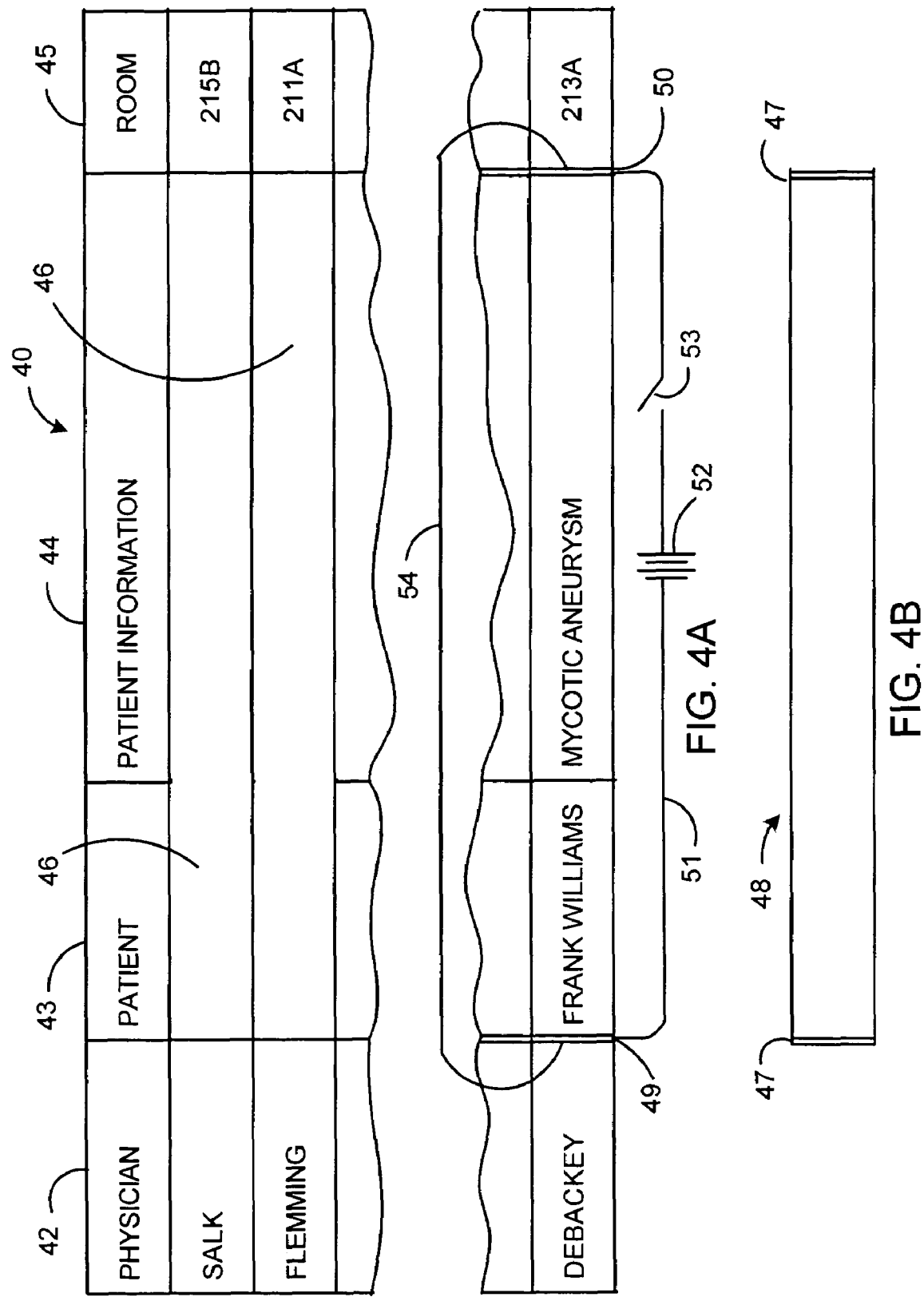

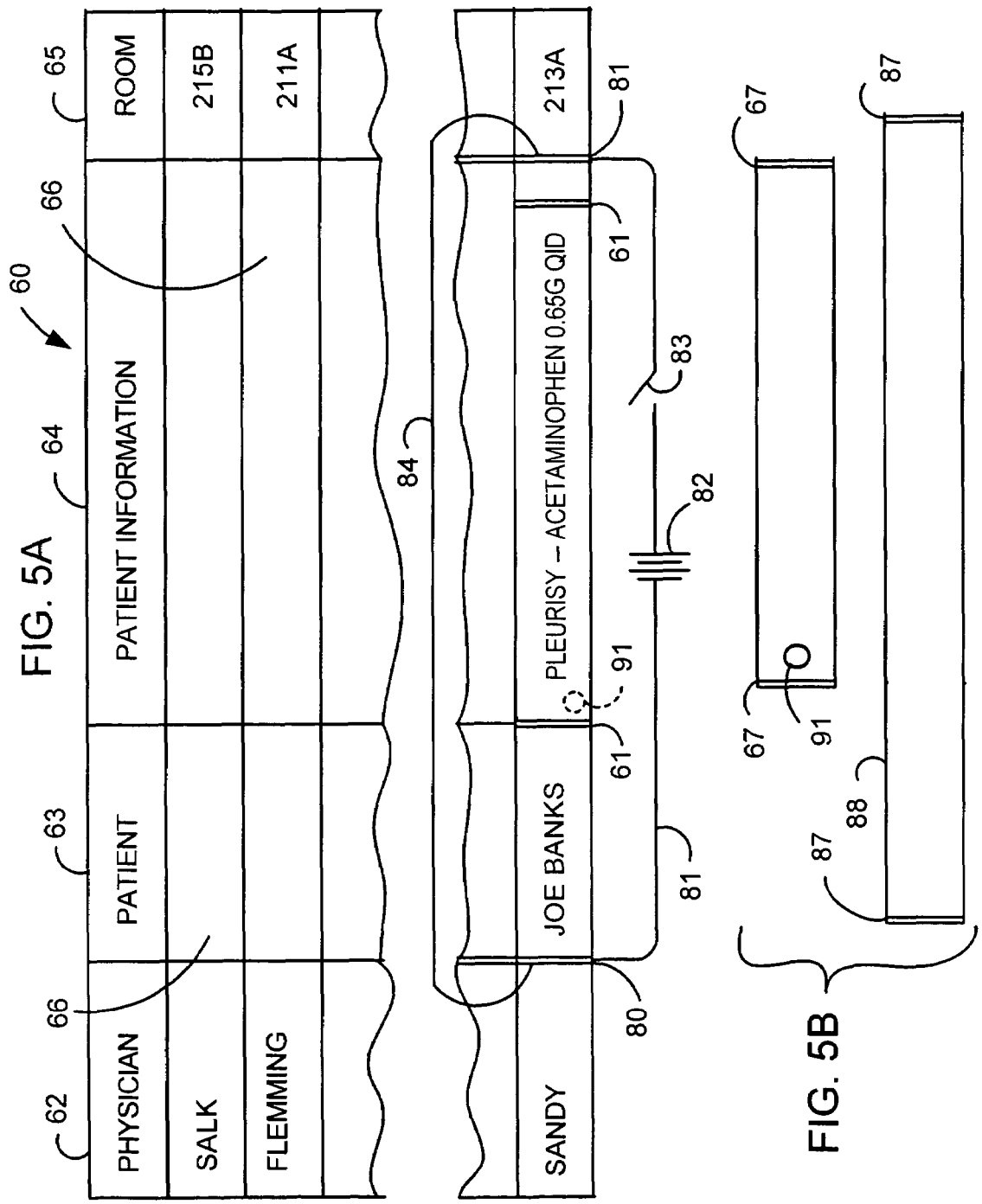

RESTRICTED ACCESS DISPLAY SYSTEM

This Application claims the benefit of the filing date of U.S. Provisional Application No. 60/630,692 filed Nov. 24, 2004, which is owned by the assignee of the present Application.

FIELD OF THE INVENTION

The invention relates generally to the field of display systems and, more particularly, to restricting access to display systems.

BACKGROUND OF THE INVENTION

Currently business, insurance companies, doctors and governments are collecting, recording and collating information about people from the time they are born to the time they die. Consequently, it has been said that we are living in the age of information. Many people are concerned that they are loosing their privacy in the information age. In order to alleviate certain invasion of privacy fears Congress has enacted and the President has signed the Health Insurance Portability and Accountability Act of 1996 (HIPAA), Pub. L. 104-191.

HIPAA requires that Federal agencies operating health plans or providing health care, State Medicaid agencies, private health plans, health care providers, and health care clearinghouses must assure their customers (for example, patients, insured individuals, providers, and health plans) that the integrity, confidentiality, and availability of protected health information they collect, maintain, use, or transmit is protected. The confidentiality of health information is threatened not only by the risk of improper access to stored information, but also by the risk of interception during electronic transmission of the information.

Before the enactment of HIPAA, a given unit of a hospital monitored a number of patients by listing the patient's name, room number, physician, and other patient information on a large board. The board usually was centrally located and easily viewed.

Thus, according to HIPPA a board may not be used in its current manner.

SUMMARY OF THE INVENTION

The present invention overcomes the problems of the prior art by modifying a board in a manner that information, i.e., the names and information about patients, or other matters, will only be seen by authorized personnel. This invention accomplishes the foregoing by placing a panel of material over the patient's name and other information concerning the patient that prevents an observer from viewing the above information. The patient's name and other information concerning the patient are revealed when authorized personnel remove the panel of material or make the panel of material translucent. The panel of material may be removed by activating a switch, entering a code, removing the material by inserting a key in a lock that keeps the material attached to the board and the panel of material may be reaffixed to the board by activating a switch, entering a code, replacing the material by inserting a key in a lock. Authorization to view patient information is controlled by limiting the personnel who have the key or code to remove the material.

This invention also supplies additional security by only permitting physicians and other authorized personnel to change the patient's diagnosis and treatment by adding or correcting information that appears on boards, i.e., whiteboards. The foregoing is accomplished by placing a translucent material over the board that may only be removed by a physician and/or other authorized personnel. Thus the physician or other authorized personnel will be the only people who will be able to change certain information appearing on boards, room panels, etc.

This invention may also be used in any environment in which only selected people may be authorized to view sensitive, proprietary, or government classified information.

BRIEF DESCRIPTION OF THE DRAWINGS

FIG. 1 is a drawing of a prior art board;

FIG. 4A is a drawing of a board in which information is hidden from observers by means of a panel that may be removed by pressing a switch;

FIG. 4B is a drawing of the back of a panel that may be placed over a portion of the information shown in the board of FIG. 4A;

FIG. 5A is a drawing of a board in which information may only be changed by a physician or otherwise authorized personnel by opening a lock to a panel 68 that does not allow observers to view certain patient information, namely the patient's diagnosis and the patient's treatment; and.

FIG. 5B is a drawing of the back panel that may be placed over the information that may be changed by a physician and the back panel that is placed over the physician information and a portion of the information shown in the board of FIG. 5A.

DETAILED DESCRIPTION OF THE PREFERRED EMBODIMENT

Figure 2A:
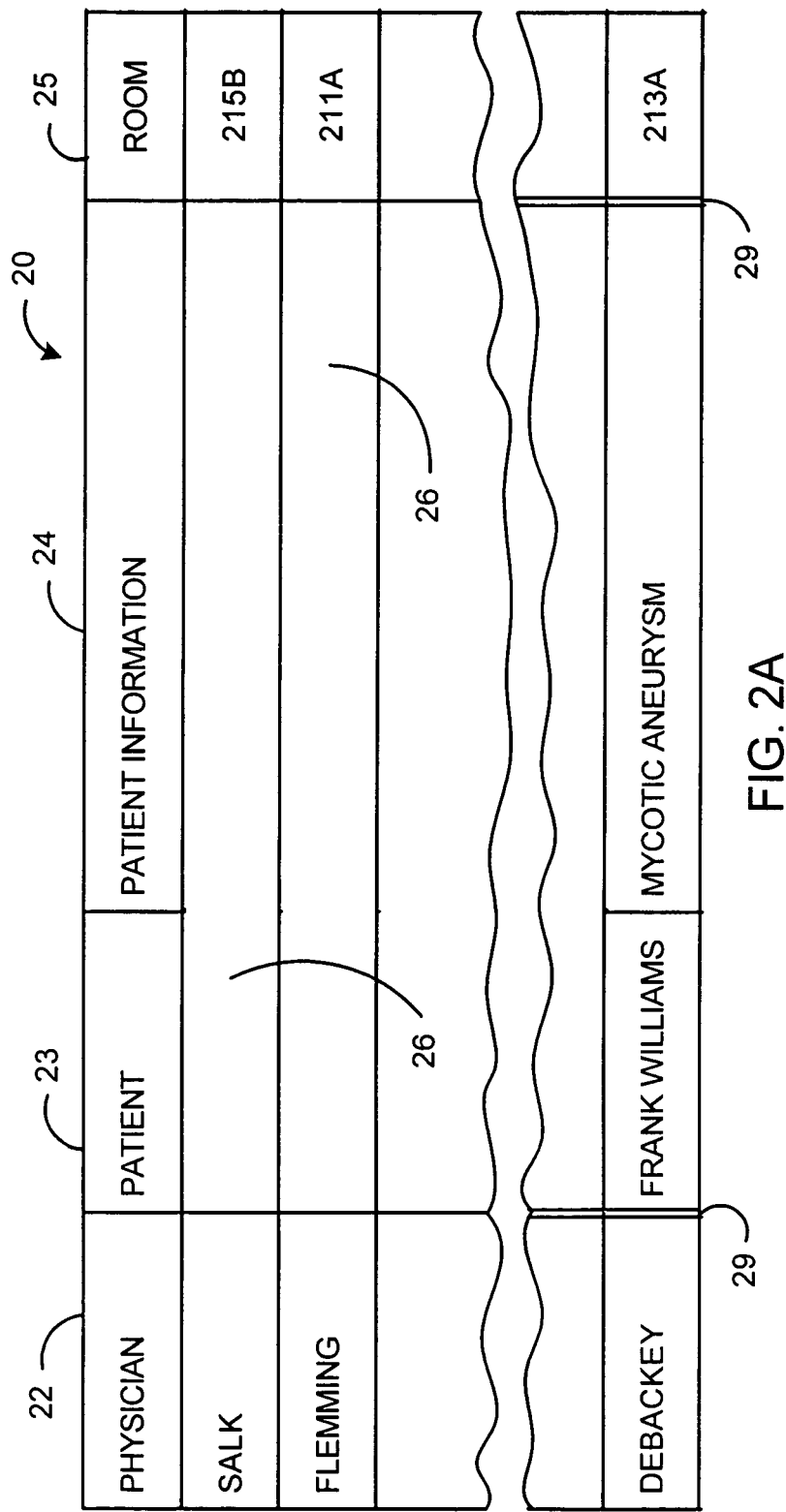
FIG. 2A is a drawing of a board in which information is hidden from observers.

Referring now to the drawings in detail, and more particularly to Prior Art FIG. 1, the reference character 11 represents a board. Information may be written on board 11 with a marking pen (not shown). For instance: the name of the attending physician may be written in column 12, the patient's name in column 13, patient information in column 14 and the patient's room number in column 15. Patient information may include the patient's diagnosis, treatment plan and other information that may be useful to the hospital staff.

FIG. 2A is a drawing of a board in which information is hidden from observers. Information may be written on board 20 with a marking pen (not shown). For instance: the name of the attending physician may be written in column 22, the patient's name in column 23, patient information in column 24 and the patient's room number in column 25. Patient information may include the patient's diagnosis and treatment plan. The patient's name that appears in column 23 and the patient information that appears in column 24 for Physicians Salk and Flemming are not currently, not observable, since panel 26 covers columns 23 and 24. Panel 26 may be made of an opaque material that is more fully described in the description of FIG. 2B. A magnet 29 is attached to board 20 so that panel 26 may be placed over and removed from columns 23 and 24. It would be obvious to one skilled in the art that panel 26 may be attached to Board 20 by hinges, hooks, vacuum, tracks and rails etc.

Figure 2B:
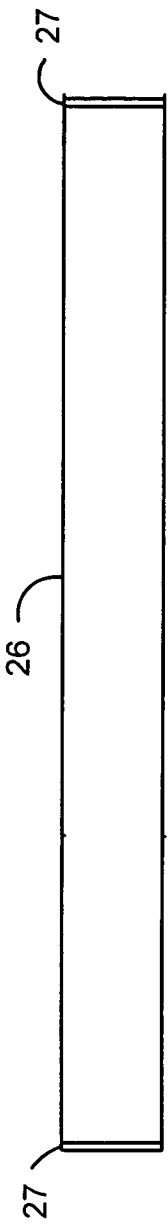
FIG. 2B is a drawing of the back of a panel that may be placed over a portion of the information shown in the board of FIG. 2B.

FIG. 2B is a drawing of the back of panel 26 that may be placed over a portion of the information shown in the board of FIG. 2B. Panel 26 has portions 27 that are made of a metallic material that will be held in position over columns 23 and 24. Panel 26 may also be a shaded material similar to those used in a two-way mirror which reveals the information on board 20 by supplying a back lighting so that a health care professional who is in a hurry will not have to remove panel 26. The health care professional will be able to view the information contained in columns 23 and 24 by being in close proximity to board 20, using a remote control device, badge reader, etc. An example of a shaded material is the see thru acrylic mirror manufactured by Plaskolite Inc. of P.O. Box 1497, Columbus, Ohio 43216. An example of a NCAP paymeric liquid crystal material that becomes transparent when power is applied the NCAP polymeric materials are manufactured by Xymox Technology Inc. of 9099 West Dean Road, Milwaukee, Wis. 53224.

Figures 3A, 3B:
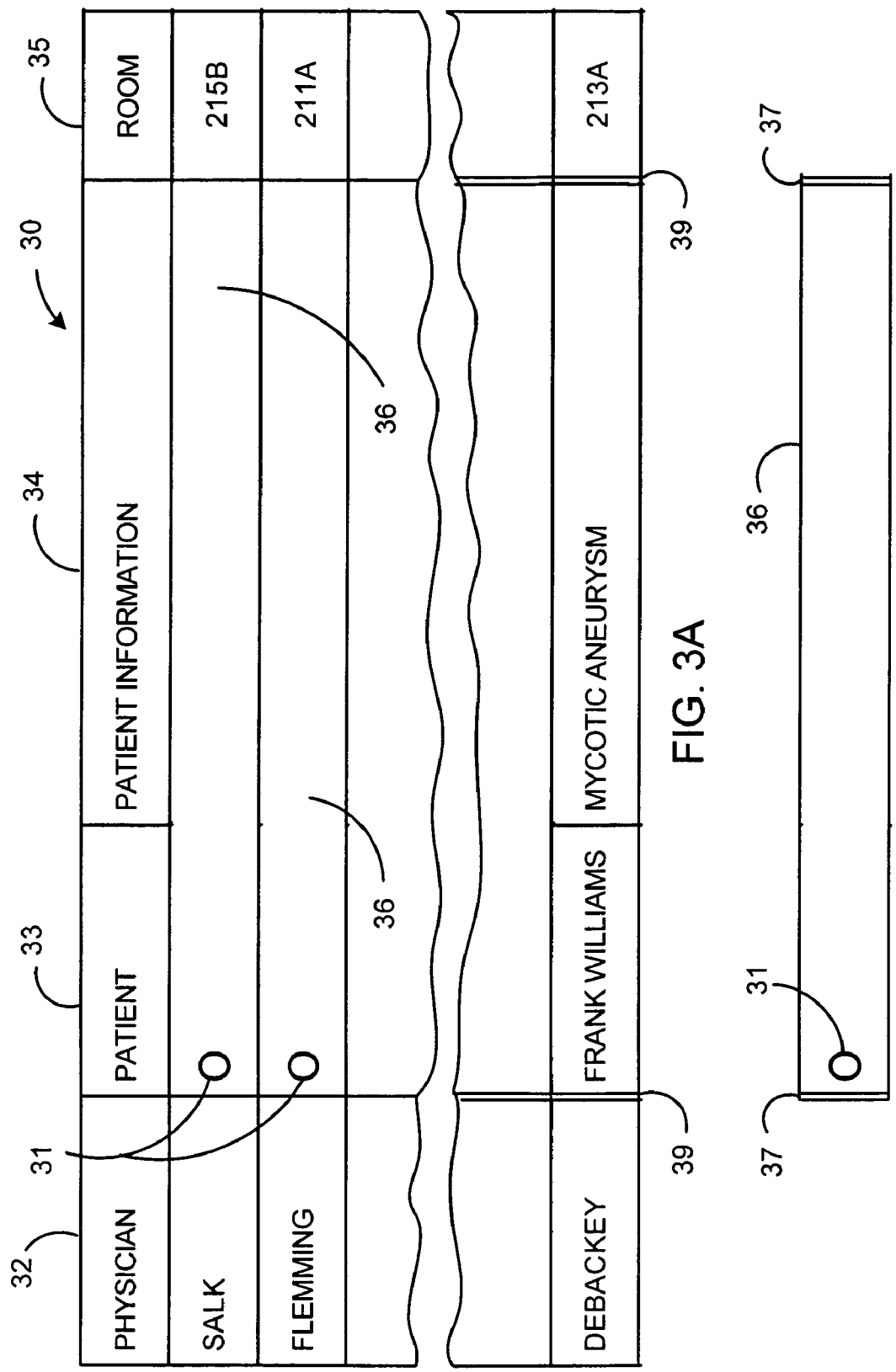
FIG. 3A is a drawing of a board in which information is hidden from observers by means of a panel that may be removed with a key.
FIG. 3B is a drawing of the back of a panel that may be placed over a portion of the information shown in the board of FIG. 3A.

FIG. 3A is a drawing of a board in which information is hidden from observers by means of a panel that may be removed with a key. Information may be written on board 30 with a marking pen (not shown). For instance: the name of the attending physician may be written in column 32, the patient's name in column 33, patient information in column 34 and the patient's room number in column 35. Patient information may include the patient's diagnosis and treatment plan. The patient's name that appears in column 33 and the patient information that appears in column 34 for Physicians Salk and Flemming are not currently, not observable, since panel 36 covers columns 33 and 34. A magnet 39 is attached to board 30 so that panel 36 may be placed over and removed from columns 33 and 34. Panel 36 is made of an opaque material that is more fully described in the description of FIG. 3B. A lock 31 is attached to board 30 so that panel 36 may be placed over and removed from columns 33 and 34 with a physical key (not shown).

Lock 31 may also be a cipher lock in which a code has to be entered to open lock 31, or a biometric device that recognizes someone's fingerprints like the Biometric Fingerprint ID manufactured by Sony Electronic, Inc. of 1 Sony Drive, Park Ridge, N.J. 07656, or a biometric device that recognizes someone's iris like the Eye Pass manufactured by Eyeticket Corp. of 3030 E. Market Street, York, Pa., 17404, or a smart card that recognizes an individual like the OMNI Heavy Duty Slot Reader manufactured by I D Tech of 10721 Walker Street, Cypress, Calif. 90630.

FIG. 3B is a drawing of the back of a panel 36 that may be placed over a portion of the information shown in the board of FIG. 3B. Panel 36 has portions 37 that are made of a metallic material that will be held in position over columns 33 and 34 when the latch portion of lock 31 is closed.

FIG. 4A is a drawing of a board in which information is hidden from observers by means of a panel that may be removed by pressing a switch. Information may be written on board 40 with a marking pen (not shown). For instance: the name of the attending physician may be written in column 42, the patient's name in column 43, patient information in column 44 and the patient's room number in column 45. Patient information may include the patient's diagnosis and treatment plan. The patient's name that appears in column 43 and the patient information that appears in column 44 for Physicians Salk and Flemming are not currently, not observable, since panels 46 covers columns 43 and 44.

Electromagnetic materials 49 and 50 are attached to board 40 so that panel 48 (FIG. 4B) may be placed over and removed from columns 43 and 44 when switch 53 is open. Wire 51 is connected to one end of electromagnetic material 49 and the other end of wire 51 is connected to one of the ends of a source of electric current 52. The other end of the source of electric current is connected to one of the terminals of switch 53. The other terminal of switch 53 is connected to electromagnetic material 50. Wire 54 is connected to the other end of material 49 and 50. Panel 46 is made of an opaque material that is more fully described in the description of FIG. 4B.

FIG. 4B is a drawing of the back of panel 48 that may be placed over a portion of the information shown in the board of FIG. 4A next to Physician Debackey. Panel 48 is an opaque material that has portions 47 that are made of a metallic material that will be held in position over columns 43 and 44 when switch 52 is closed.

FIG. 5A is a drawing of a board in which information may only be changed by a physician or otherwise authorized personnel by opening a lock to a panel 68 that does not allow observers to view certain patient information, namely the patient's diagnosis and the patient's treatment. Information may be written on board 60 with a marking pen (not shown). For instance: the name of the attending physician may be written in column 62, the patient's name in column 63, patient information in column 64 and the patient's room number in column 65. Patient information may include the patient's diagnosis and treatment plan, which may only be changed by a physician or other authorized personnel. The patient's name that appears in column 63 and the patient information that appears in column 64 for Physicians Salk and Flemming are not currently, not observable, since panels 66 cover columns 63 and 64.

Magnets 61 are attached to board 60 so that translucent panel 68 may be placed over and removed from column 64 by unlocking lock 91. Panel 68 is more fully described in the description of FIG. 5B. A lock 91 is attached to board 60 so that panel 68 may be placed over and removed from column 64 with a physical key (not shown) to enable a physician to write the diagnosis and treatment on board 60 with a marking pen (not shown) for their patient. Lock 91 may also be a cipher lock in which a code has to be entered to open lock 91, or a biometric device that recognizes someone's fingerprints or a biometric device that recognizes the individual or a smart card that recognizes an individual.

Electromagnetic materials 80 and 87 are attached to board 60 so that panel 88 (FIG. 5B) may be placed over and removed from columns 63 and 64 when switch 83 is open. Wire 81 is connected to one end of electromagnetic material 80 and the other end of wire 81 is connected to one of the ends of a source of electric current 82. The other end of the source of electric current is connected to one of the terminals of switch 83. The other terminal of switch 83 is connected to electromagnetic material 87. Wire 84 is connected to the other end of materials 80 and 87. Panel 88 is made of an opaque material that is more fully described in the description of FIG. 5B.

FIG. 5B is a drawing of the back of panel 68 that may be placed over the information that may be changed by a physician and the back of panel 88 that is placed over the physician information and a portion of the information shown in the board 60 of FIG. 5A. Panel 68 has portions 67 that are made of a metallic material that will be held in position over column 64 when the latch portion of lock 91 is closed. Panel 88 is an opaque material that has portions 87 that are made of a metallic material that will be held in position over columns 63 and 64 (FIG. 5A) when switch 82 is closed.

Figure 6:
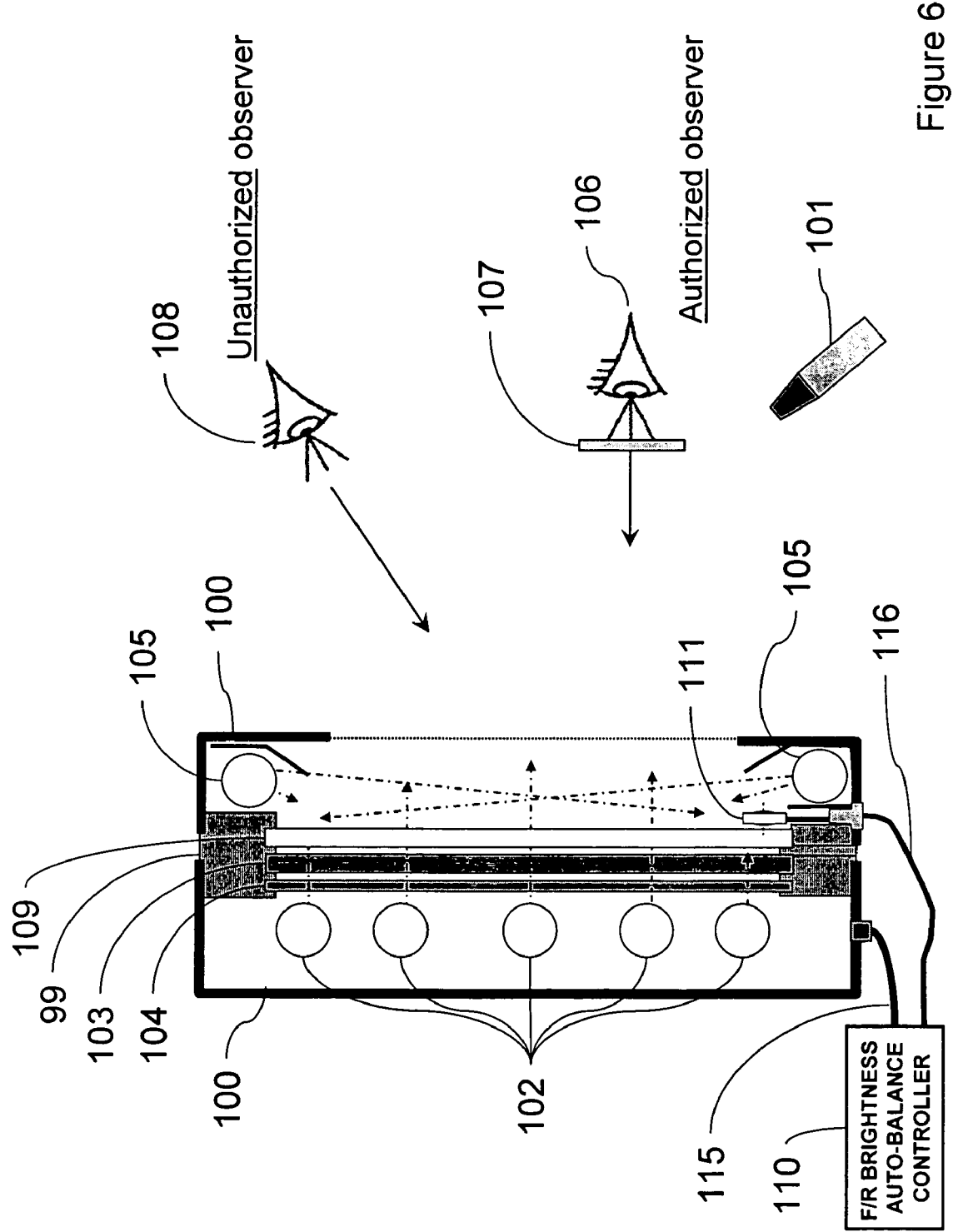
FIG. 6 is a drawing of a clear glass board that is mounted in a housing 100 in which information is hidden from observers by means of illuminating the board with white light and polarizing the white light.

FIG. 6 is a drawing of a clear glass board that is mounted in a housing 100 in which information is hidden from observers by means of back illuminating the board with white light and polarizing the white light. Clear glass board 109 is similar to opaque board 20. The same type of information that is written in columns 22, 23 and 24 of FIG. 2A may be written on a clear piece of glass 109 that is attached to housing 100 by holder 99, which is attached to housing 100. Holder 99 supports board 109, polarizer 103 and diffuser 104 in housing 100. White marker 101 may be used to write information on board 109. White marker 101 may be the Staedtler white liquid chalk marker manufactured by The Essentials Company of April House, Davey Lane, Charsfield, Woodbridge, Suffolk IP13 7QG U.K.

White light lamp bank 102 is placed behind diffuser 104 in a manner that the information written on board 100 will be back illuminated by light 102. Diffuser 104 will diffuse the light produced by white lights 102 to make board 109 appear uniformly white. Diffuser 104 may be a plate of ground glass that diffuses the light. A polarizer 103, that is neutral in color, is placed directly in front of diffuser 104 and behind board 109 with its plane of polarization oriented in the vertical plane. Polarizer 103 will limit the polarization of the light received from diffuser 104 so that an observer 108 sees only vertically polarized light and an observer 106 who is wearing horizontally polarized glasses 107 will not see the diffused light component at all. Thus, observer 108 will see board 109 as a bright white screen and observer 106 wearing glasses 107 will see board 109 as a black screen. Polarizer 103 may be the 5511 model sheet polarizer, manufactured by New Focus, Inc. of 2630 Walsh Avenue, Santa Clara, Calif. 95051.

A clear piece of glass 109 is placed in front of polarizer 103 in order to provide an erasable surface to write information on board 109 with white marker 101. Lamp array 105 illuminates the front surface of board 109 and the information that is written on board 109 with marker 101. Adjustment balance 110 is provided to vary the relative illumination between lamp bank 102 and lamp array 105 to render the writing on board 109 invisible to some one who is not wearing glasses 107. Cable 115 connects controller 110 to lamp array 105 and lamp bank 102 and cable 116 connects controller 110 to dual light sensor 111. The adjustment may be manually performed or automated by the use of a dual sensor 111 that monitors the illumination component from lamps 105 and the light being emitted from polarizer 103 and diffuser 104. The dual light sensor 111 has two matched sensors one looking forward, the other looking back towards polarizer 103. Observer 108 when looking at board 109 will see bright written alphanumeric characters against a n equally bright white background rendering the information written on board 109 with marker 101 invisible. Observer 106 wearing glasses 107 sees white characters against a black background and is able to read the alphanumeric characters written on board 109 with marker 101.

If the polarizer 103 used is not "neutral" in color and in fact has a color "tint" there is the possibility that the color difference between the tinted back light source (lamp bank 102) and the and the "white" lamp array 105 may produce a large enough color tint difference to reach the threshold of visual perception. To prevent the foregoing one may pre-tint lamp array 105 to approximate the tint of polarizer 103.

Figure 7:
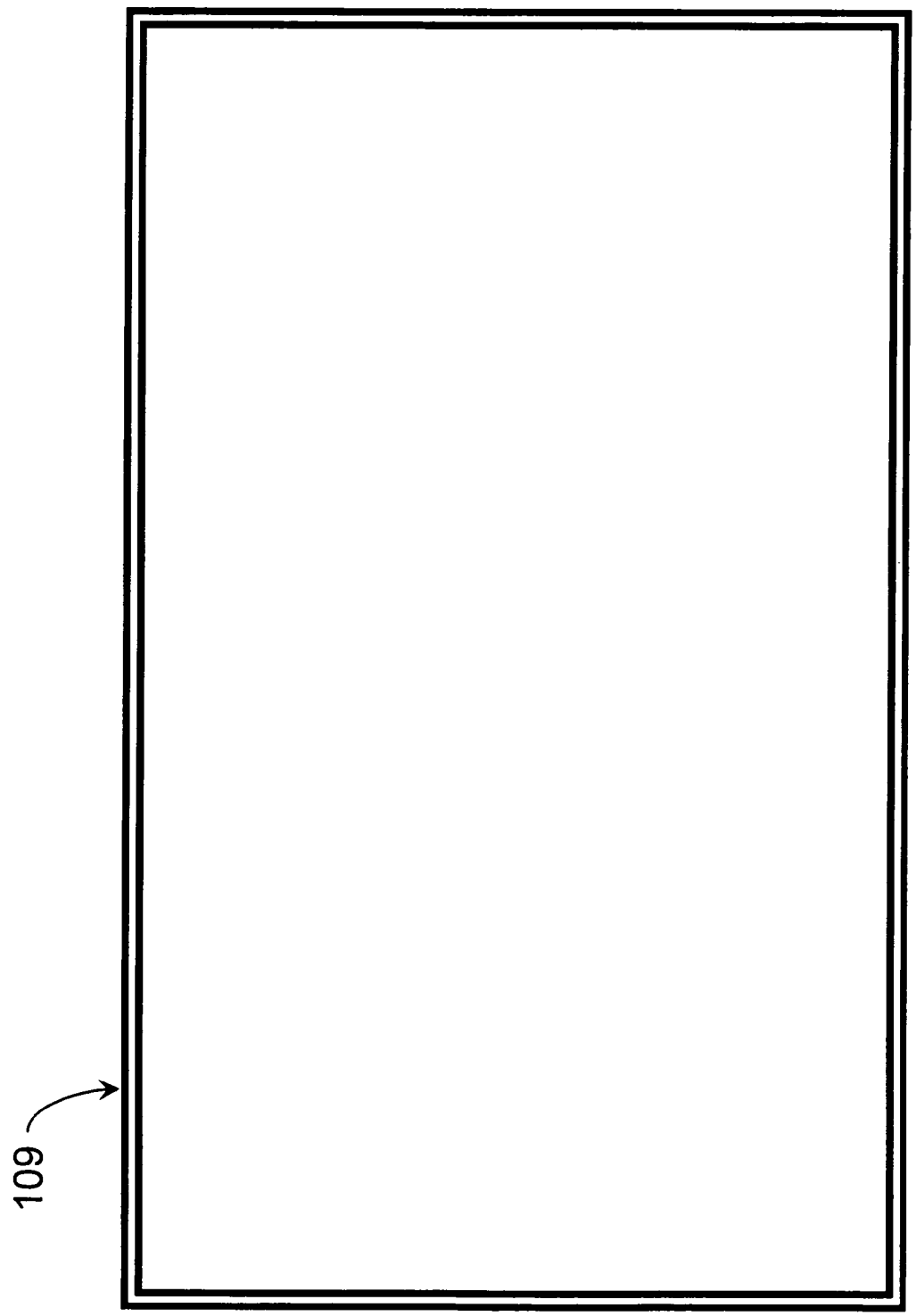
FIG. 7 is a drawing of board 109 of FIG. 6, as seen by an observer who is not using glasses 107 to view board 109.

Polarizer glasses 107 may be ordinary polarizied glasses with the plane of polarization rotated 90 degrees from the orientation of normal polarized sunglasses FIG. 7 is a drawing of board 109 of FIG. 6, as seen by an observer who is not using glasses 107 to view board 100. Observer 106 will see board 109 as a white screen with nothing written on it.

Figure 8:
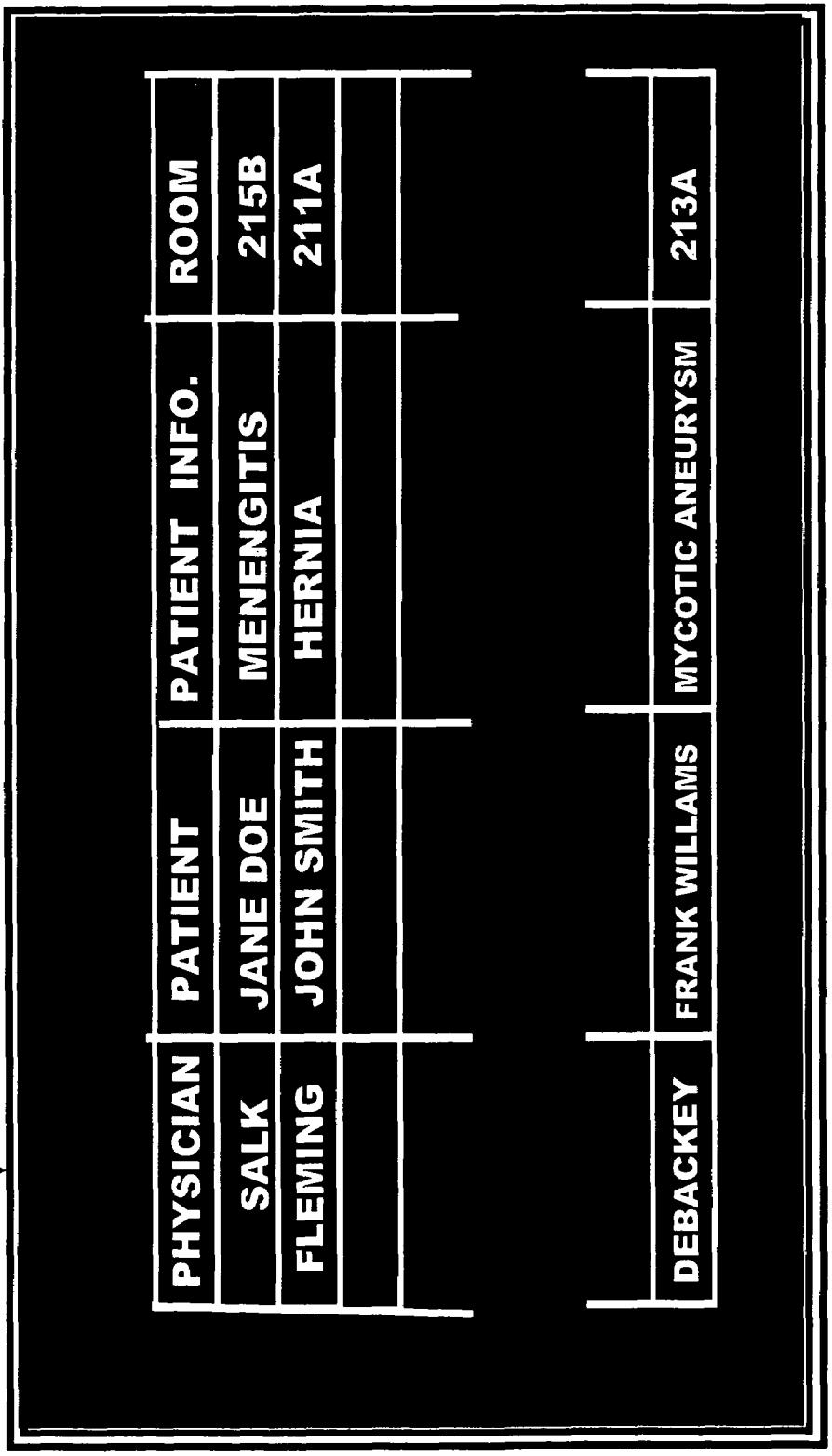
FIG. 8 is a drawing of board 109 of FIG. 6, as seen by an observer who is using glasses 107 to view board 109.

FIG. 8 is a drawing of board 109 of FIG. 6, as seen by an observer who is using glasses 107 to view board 100. Board 109 will appear black to the observer and the observer will see the information written on board 109 with marker 101 in white. Observer 108 will see board 109 as a black screen with the marker 101 produced white information written thereon.

The above specification describes a new and improved method for restricting access to material that is placed on a board. It is realized that the above description may indicate to those skilled in the art additional ways in which the principles of this invention may be used without departing from the spirit. Therefore, it is intended that this invention be limited only by the scope of the appended claims.

What is claimed is:

1. A method for restricting access to information that is written in a color having predetermined wavelengths on a clear material that comprising the steps of:
   (a) applying polarized light having the predetermined wavelengths in a specified plane to a back of a clear material;
   (b) illuminating a front of the clear material with light; having the predetermined wavelengths;
   (c) adjusting the light illuminating the back of the clear material and the light illuminating the front of the clear material so that the information written on the material will have the same illumination and will be invisible to a observer; and
   (d) polarizing the white light emanating from the material so that a designated observer will be able to view the information written on the material.

2. The method claimed in claim 1, further including the step of:
   diffusing the polarized applied light before the light reaches the back of the clear material.

3. The method claimed in claim 1, wherein the predetermined wavelengths are the wavelengths of white light.

4. The method claimed in claim 1, wherein the material is glass.

5. The method claimed in claim 1, wherein the material is plastic.

6. The method claimed in claim 1, wherein the polarized light emanating from the material is polarized by a polarizing lens that is placed in a eye glass frame.

7. The method claimed in claim 1, wherein the light illumination of the back and the front of the clear material is manually adjusted.

8. The method claimed in claim 1, wherein the light illumination of the back and the front of the clear material is automatically adjusted.

9. The method claimed in claim 1, wherein the polarizer in step (a) has a neutral tint.

* * * * *